United States Patent [19]

Boynton et al.

[11] Patent Number: 5,175,156

[45] Date of Patent: Dec. 29, 1992

[54] CHROMIC PICOLINATE TREATMENT

[75] Inventors: Herb Boynton, La Jolla, Calif.; Gary W. Evans, Puposky, Minn.

[73] Assignee: Nutrition 21, San Diego, Calif.

[21] Appl. No.: 807,058

[22] Filed: Dec. 9, 1991

Related U.S. Application Data

[60] Division of Ser. No. 326,590, Mar. 21, 1989, Pat. No. 5,087,623, which is a continuation-in-part of Ser. No. 200,390, May 31, 1988, abandoned, which is a continuation-in-part of Ser. No. 126,588, Nov. 30, 1987, abandoned.

[51] Int. Cl.⁵ .......................................... A61K 31/555
[52] U.S. Cl. ................................. 514/188; 514/824
[58] Field of Search ............................... 514/188, 824

[56] References Cited

U.S. PATENT DOCUMENTS 4,315,927  2/1982  Evans ................................. 514/188
4,343,905  8/1982  Szalay ................................ 5.4/188

OTHER PUBLICATIONS

*Present Knowledge in Nutrition*, 5th Ed. The Nutrition Foundation (1984) pp. 571–582.
Boyle, et al., Southern Med., Jour. 70:1449–1453 (1977).
Anderson, R. W., Clin. Physiol. Biochem. 4:31–41 (1986).
Riales, R., in *Chromium in Nutrition and Metabolism*, Shapcott and Hybert, Eds., pp. 199–212 (1979).
Newman, H. A. I., et al., Clin. Chem. 24:541–544 (1978).
*The Lipid Research Clinics Coronary Primary Prevention Trial Results*, J.A.M.A. (J. Amer. Med. Assn.) 251:351–364 (1984).
*Recommended Dietary Alowances*, 9th Revised Ed., The National Academy of Sciences p. 159–161 (1980).
Albers, J. J., et al., Clin. Chem. 24:853–856 (1978).
Friedewald, W. T., Clin. Chem. 18:499–502 (1972).
Naito, H. K., J. Clin. Immunoassay 9:11–20 (1986).
Clegg, M. D. and Schroeder, W. A., J. Amer. Chem. Soc. 81:6065–6069 (1959).
Hills, M., et al., Brit. Jour. Clin. Pharmacol. 8:7–20 (1979).

Newman, W. P., et al., New England J. of Med. 314:138–144 (1986).
Avogaro, P., et al., Artery 4:385–394 (1978).
Sniderman, A., et al., Proc. Natl. Acad. Sci. U.S.A. 77:604–608 (1980).
Riesen, W. F., et al., Atherosclerosis 37:157–162 (1980).
De Backer, G., et al., Atherosclerosis 42:197–203 (1982).
Maciejko, J. J., et al., New Engl. J. Med. 309:385–389 (1983).
Schmidt, S. B., et al., Am. J. Cardio. 55:1459–1462 (1985).
Press, R. I., et al. Western Journal of Medicine 12:41–45 (1990).
Kwiterovich, P. O., et al., Preventive Medicine 12:815–834 (1983).
Brunzell, J. D. et al., Atherosclerosis 4:79–83 (1984).
Evans, G. W., et al., International Journal of Biosocial and Medical Research 11(2): 163–180 (1989).
Anderson, R. A. et al., Amer. J. Clin. Nutr. 41:1177–1183 (1985).

(List continued on next page.)

*Primary Examiner*—Frederick E. Waddell
*Assistant Examiner*—Raymond J. Henley, III
*Attorney, Agent, or Firm*—Knobbe, Martens, Olson & Bear

[57] ABSTRACT

The administration of chromic picolinate, preferably in the form of chromic tripicolinate, as a prophylactic or therapeutic agent for controlling various blood serum parameters. In particular, the administration is for controlling blood serum lipid levels, including the lowering of undesirably high blood serum LDL-cholesterol levels and the raising of blood serum HDL-cholesterol levels. Additionally, the administration is for controlling undesirable high blood serum glucose levels, this being particularly applicable for the treatment of maturity-onset diabetes. Additionally, chromic picolinate, preferably in the form of chromic tripicolinate, is administered to facilitate uptake of amino acids by skeletal muscle. Thus chromic picolinate can act as an effective anabolic agent.

31 Claims, 7 Drawing Sheets

OTHER PUBLICATIONS

Scahller, K. H., At Absorption Newsletter 12:147–150 (1973).
Evans, G. W., Pediatric Res. 14:876–880 (1980).
Offenbacher, E. G. and Pi-Sunyer, F. X., Ann Rev. Nutr. 8:543–563 (1988).
Seal, C. J. and Heaton, F. W., (1983) Brit. Journal of Nutrition 50:317–324.
Chemical Abstracts Citation 88:163086, Russian Publication (1977).
Toepfer, E. W. et al., J. Agr. Food Chem. 21(1): 69–73 (1973).
McCarthy, M. F. Medical Hypothesis 6:1177–1189, (1980).
Anderson, R. A., et al., Metabolism 32(9):894–899 (1983).
Offenbacher, E. G., et al., Diabetes 29:919–925 (1980).
Elwood, J. C., et al., J. Amer. Coll. of Nutri. 1:263–274 (1982).
Abraham, A., et al., The Amer. J. of Clin. Nutri. 33:2294–2298 (1980).
Simonoff, M., et al., Biolog. Trace Element Res. 6:431–439 (1984).
NIH Report of Plasma Lipid Distribution in Selected North American Populations (1984).
Anderson, R. "Trace Elements in Health and Disease" Skandia Symposia Oct. 23–25, 1984, pp. 110–119.
Chen, N. J. Nutr. 103:1182–1186 (1973).
Davidson, I., et al. Proc. Soc. Exp. Med. Biol. 127:66–70 (1967).
Gonzales-Vergara, E., et al. Israel Journal of Chemistry 21:18–22 (1981).
Mirsky, N. Journal of Inorganic Biochemistry 13:11–21 (1980).
Tuman, R. Diabetes 27:49–56 (1978).
Yamamoto, A. Toxicology and Applied Pharmacology 59:515–523 (1981).
Yamamoto, A., et al. Jour. of Inorganic Biochemistry 22:91–102 (1984).
Nutrition 21 Consumer Education Brochure: "The Prophylactic and Therapeutic Potential of Chromium Picolinate in Diabetes, Hyperlipidemia, Anabolism and Weight Reduction" (1989).

ized by a disturbance of glucose, lipid, and protein metabolism and by a shortened life span. Chromium is essential for optimal insulin activity in all known insulin-dependent systems. Boyle et al., *Southern Med. J.* 70: p. 1449–1453 (1977) at 1450. Insufficient dietary chromium has been linked both to maturity-onset diabetes and to cardiovascular diseases.

CHROMIC PICOLINATE TREATMENT

CROSS-REFERENCE TO RELATED APPLICATIONS

This application is a divisional of U.S. patent application Ser. No. 07/326,590, filed Mar. 31, 1989, now U.S. Pat. No. 5,087,623, which is a continuation-in-part of U.S patent application Ser. No. 07/200,390 entitled "Chromic Picolinate Treatment," filed May 31, 1988, now abandoned which is a continuation-in-part of U.S. patent application Ser. No. 07/126,588, entitled "Chromic Picolinate Treatment," filed Nov. 30, 1987 now abandoned.

FIELD OF THE INVENTION

The field of the invention is nutritional trace elements and, more specifically, chromium compounds.

DESCRIPTION OF RELATED ART AND INTRODUCTION TO THE INVENTION

Heart disease, more specifically, atherosclerotic heart disease, is a leading cause of death in the United States. High serum cholesterol has been unequivocally established as a major risk factor for heart disease. Notwithstanding this knowledge, millions of Americans and others around the world have cholesterol levels in the high risk range. Often these cholesterol levels are resistant to conventional dietary modification, i.e., a reduction in dietary saturated fat and cholesterol.

Diabetes is known to afflict at least 10 million Americans, and millions more may have the disease without knowing it. In the form of this disease known as maturity-onset diabetes (as opposed to juvenile diabetes), the pancreas often continues to secrete normal amounts of insulin, but this insulin is ineffective in preventing the symptoms of diabetes which include hyperglycemia, impaired carbohydrate metabolism, glycosuria, and decreased insulin sensitivity.

Chromium is a nutritionally essential trace element, as are iron, iodine, copper and zinc, among others. The essentiality of chromium in the diet was established in 1959 by Schwarz, as cited in *Present Knowledge in Nutrition*, page 571, Fifth Edition (1984, The Nutrition Foundation, Washington, D.C., U.S.A.). This reference, and all others referred to herein, are hereby incorporated by reference. Schwarz placed mice on a highly purified diet that excluded chromium. The mice became "glucose intolerant" and, thus, were no longer able to metabolize glucose (blood sugar) normally. The mice developed symptoms identical to non-insulin dependent diabetes. When chromium was restored to the diet via brewer's yeast, normal glucose metabolism was restored. Schwarz named the unknown chromium-dependent molecule responsible for the restoration of normal glucose metabolism the "Glucose Tolerance Factor" ("GTF").

Chromium depletion is characterized in animals by disturbance of glucose, lipid, and protein metabolism and by a shortened life span. Chromium is essential for optimal insulin activity in all known insulin-dependent systems. Boyle et al., *Southern Med. J.* 70: p. 1449–1453 (1977) at 1450. Insufficient dietary chromium has been linked both to maturity-onset diabetes and to cardiovascular diseases.

The principle energy sources for the body are glucose and fatty acids. Chromium depletion results in biologically ineffective insulin and a compromised glucose metabolism, and the body must then rely primarily on lipid metabolism to meet energy requirements. Such individuals produce excessive amounts of acetyl-CoA and ketone bodies. Part of the accumulated acetyl-CoA is diverted to increased cholesterol biosynthesis, thus resulting in hypercholesterolemia. Diabetes mellitus is manifested in large measure by glycosuria, hypercholesterolemia, and often, ketoacidosis. The accelerated atherosclerotic process seen in diabetics, it has been noted, is associated with hypercholesterolemia. Boyle et al., supra.

Studies conducted by the U.S. Department of Agriculture show that the dietary chromium intake of most individuals, though, is considerably less than the suggested safe and adequate intake. It has also been concluded that the suboptimal dietary intake of chromium is exacerbated by increased chromium losses due to stress and, furthermore, that certain refined foods which include simple sugars enhance chromium losses. Supplementation of chromium to normal individuals has been reported to lead to improvements in glucose tolerance, serum lipid concentrations, including high-density lipoprotein cholesterol, insulin and insulin binding. Anderson, *Clin. Physiol. Biochem.* 4:31–41 (1986). Supplemental chromium in the trivalent form, e.g., chromic chloride, is associated with improvements of risk factors associated with maturity-onset diabetes and cardiovascular diseases.

Chromium, in the form of GTF, is known to function as a co-factor for the hormone insulin. It binds to insulin and potentiates many, and perhaps all, of the functions of insulin. Boyle et al, supra. These functions include, but are not limited to, the regulation of carbohydrate and lipid (fat) metabolism. *Present Knowledge In Nutrition*, supra, at p. 573–77.

Introducing inorganic chromium compounds per se into individuals is, however, not particularly beneficial. Chromium must be converted endogenously into an organic complex or it must be consumed as a biologically active molecule. Only about 0.5% of ingested inorganic chromium is assimilated in the body. "Recommended Dietary Allowances," page 160, 9th Revised Edition (1980, The National Academy of Sciences). Only 1–2% of most chromium is assimilated while 10–25% of chromium in brewer's yeast is assimilated. *Present Knowledge In Nutrition*, supra at p. 582. This is probably due to the fact that, as we have discovered, much of the chromium in brewer's yeast is in the form of GTF.

The results of a study have been published describing an investigation into the effects of brewer's yeast on lipoprotein cholesterol concentrations in a group of male volunteers. The study was initiated based upon reports that chromium, or brewer's yeast (which is rich in the chromium-containing compound GTF), could lower serum total cholesterol. Riales, "Chromium in Nutrition and Metabolism" p. 199 (Shapcott & Hubert, Eds.) (1979). It was concluded that there was an increase in HDL-cholesterol concentration, the beneficial form of cholesterol. It has also been reported that groups of the population with coronary artery disease have significantly lower serum chromium concentrations than groups of the population having normally unobstructed arteries. Newman et al., *Clin. Chem.* 24:541 (1978).

In U.S. Pat. No. 4,315,927, issued on Feb. 16, 1982, to Gary W. Evans for "Dietary Supplementation With Essential Metal Picolinates." Evans describes the discovery that when selected essential metals are administered to mammals as exogenously synthesized coordination complexes of picolinic acid, they are directly available for absorption into the system without competition from other metals. That patent describes one object of the invention to be the ability to provide a composition and method for selectively supplementing the essential metals in the diets of humans and mammalian animals and for facilitating absorption of these metals by the intestinal cells. Other described objects of the invention include the correction of predetermined metal deficiencies in mammals, the elimination of symptoms of those deficiencies without concurrently reducing the assimilated levels of other essential metals, and the administration of trace metals in a safe, physiological form which is simple to produce and economically feasible to distribute on a commercial basis. The exogenously synthesized essential metal coordination complexes of picolinic acid (pyridine-2-carboxylic acid) for use in the invention of U.S. Pat. No. 4,315,927 are characterized by the following structural formula:

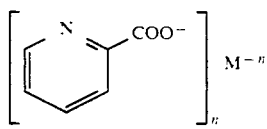

Wherein M represents the metallic cation and n is equal to the cation's valence. When $M^n$ ("chromic" as used in this application) is $C^{-3}$ and $n=3$ then the compound is chromic tripicolinate. Other chromium picolinates could include $M=Cr^{-3}$ and $n=2$ ("chromic dipicolinate") or $n=1$ ("chromic monopicolinate"), each with additional amions present. The patent states that the particular trace elements of interest are zinc, iron, and chromium, although the patent also mentions copper, cobalt, and manganese. The patent further describes methods for preparation of metal picolinates, including zinc, copper, iron and chromium.

Plasma cholesterol and triglycerides are transported in lipoproteins. Hyperlipoproteinemias are conditions in which the concentrations of these cholesterol- or triglyceride-carrying lipoproteins exceed the normal limit. Clinical concern arises because an elevated concentration of lipoproteins can accelerate the development of atherosclerosis, with the secondary possibilities of thrombosis and infarction. About half of the deaths in the United States are a result of such events Recent work suggests that reduction of lipoprotein concentrations in plasma can diminish the increased risk of atherosclerosis that accompanies hyperlipoproteinemia.

The hyperlipoproteinemias have been designated as either primary or secondary. Secondary hyperlipoproteinemias are complications of a more generalized metabolic disturbance, such as diabetes mellitus or excessive intake of ethanol. The primary hyperlipoproteinemias are typically caused either by an inherited single-gene defect (monogenic hyperlipoproteinemias) or a combination of multiple subtle genetic factors that act together with environmental ones (multifactorial or polygenic hyperlipoproteinemias).

Much circumstantial evidence exists that treatment of hyperlipoproteinemia will diminish or prevent atherosclerotic complications. For example, numerous populations studies have shown that an elevated concentration of total cholesterol or LDL- cholesterol in plasma constitutes a major risk factor for the occurrence of atherosclerotic events. In the case of monogenic disorders, family studies have documented a markedly increased risk of vascular disease among affected members. Until recently, however, treatment of hyperlipoproteinemia was a controversial issue, primarily because the lowering of plasma lipids had not been shown to prolong life or diminish the clinical complications of atherosclerosis.

In 1984, results of the Lipid Research Clinic's Coronary Primary Prevention trial, a multi-center, randomized, double-blind study, provided strong evidence that a reduction in plasma concentrations of LDL-cholesterol can reduce the risk of coronary heart disease. Lipid Research Clinic's Program, "The lipid research clinic's coronary primary prevention trial results," J.A.M.A. 251:351-374 (1984). Analysis of the relationship between reduction of cholesterol and coronary heart disease suggests that the incidence of coronary heart disease in patients with hyperlipoproteinemia would be reduced by nearly 50% for individuals who achieved a 25% reduction in plasma total cholesterol or a 35% fall in plasma LDL-cholesterol.

In view of the incidence of heart disease in the United States and around the world, and the high incidence of undesirable blood cholesterol and triglyoeride levels which can lead to heart disease and other disorders, it would be desirable to have a simple way of lowering undesirable blood lipid levels. Described herein is the use of chromic picolinate compounds, preferably chromic tripicolinate, to prevent and treat undesirable levels of blood cholesterol, as well as to control symptoms associated with maturity-onset diabetes.

It is also known that anabolic agents, such as some steroids, can be used by individuals to promote an increase in lean body mass, probably by decreasing serum amino acid levels. Anabolic steroids, though, are known to have serious side effects when taken over prolonged periods. It would therefore also be desirable to have an alternative to agents such as anabolic steroids which can promote an increase in lean body mass.

SUMMARY OF THE INVENTION

Ingested chromium can combine with picolinic acid, which is made in the body, to form chromic picolinate. As noted, however, chromium is not easily metabolized. We have discovered that chromic tripicolinate occurs in brewer's yeast and has Glucose Tolerance Factor activity. We have also discovered that chromic picolinate, preferably chromic tripicolinate, can be used to prevent and relieve undesirably high levels of lipids, including LDL-cholesterol, glucose, and products formed as a result of high levels of glucose, such as glycosylated hemoglobin in the blood. Furthermore, we have also discovered that chromic picolinate, preferably chromic tripicolinate, can be used as a therapeutic agent to relieve some of the symptoms of maturity-onset diabetes and reduce the need for exogenous insulin and/or other hypoglycemic agents, such as the sulfonylureas. Additionally it has been discovered that chromic picolinate, preferably chromic tripicolinate, can be used as an anabolic agent to increase lean body mass. It is expected that chromic picolinate, and in particular chromic tripicolinate, can be used in the dosage range corresponding to about 10 to about 500 micrograms of chromium per day for the above indications.

DRAWINGS

Embodiments of the invention are described with reference to the drawings in which.

DETAILED DESCRIPTION OF THE INVENTION

Figure 1:
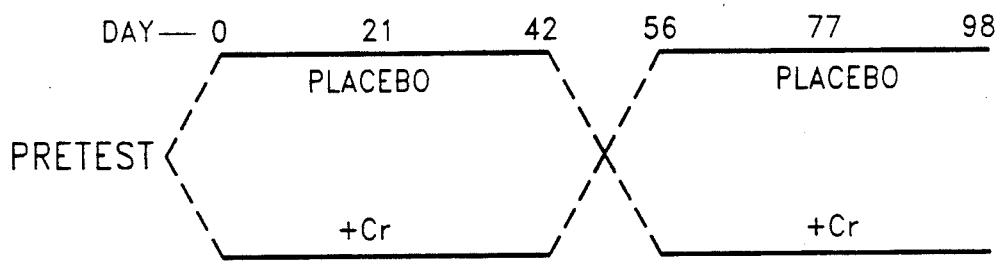
FIG. 1 illustrates the design of the human study of EXAMPLE 3 (described below).

We have identified picolinic acid as a natural component of brewer's yeast and have discovered that chromic tripicolinate is a highly assimilable, biologically-active form of chromium that binds to insulin and insulin receptors. We have further discovered that, in fact, chromic tripicolinate is a biologically-active form of chromium or, stated another way, it has Glucose Tolerance Factor activity.

Chromic tripicolinate, because of its assimilability and because it will bind to insulin and insulin receptors, is capable of enhancing the normal functions of insulin, which include:

a. reduction of elevated serum cholesterol;
b. improvement of glucose tolerance; and
c. reduction in fasting hyperglycemia.

The "recommended" or "safe and adequate" intake of chromium has been established by the National Academy of Sciences as 50-200 micrograms daily. *Recommended Dietary Allowances,* pp. 159-161, Ninth Edition (1980, National Academy of Sciences). Because chromic tripicolinate is assimilated more readily, as we have shown below, and will be more effective for the uses disclosed herein than other compounds of chromium, a lesser amount of chromic tripicolinate may be required for such uses i.e., the prophylactic function of preventing or reducing serum lipids, total serum cholesterol and LDL-cholesterol, and the therapeutic function of alleviating the symptoms of maturity-onset diabetes.

EXAMPLE 1

This Example illustrates the far greater increased rate of absorbtion of chromic tripicolinate over an inorganic chromium salt (chromic chloride), in a mammal.

Protocol

In this example, chromic tripicolinate was first synthesized by combining 3.66 grams of picolinic acid (Sigma Chemical, St. Louis) and 2.66 grams of chromic chloride with 20 ml. of deionized water. The solution was heated with stirring for 15 minutes after which the contents were placed in a refrigerator overnight to obtain maximum crystalization. The supernatant was removed by vacuum filtration followed by recrystalization from hot deionized water. To synthesize chromic (chromium-51) tripicolinate, 0.12 micromoles recrystalized picolinic acid was added to a solution containing 0.03 micromoles of chromic ($Cr^{51}$) chloride in 5.0 ml. acetate buffer, pH 5.0. The solution was stirred for 30 minutes at 90° C., cooled and subsequently reheated for 30 minutes at 90° C. The solution was cooled to room temperature before use.

Each of four male Sprague-Dawley rats weighing 125-150g was given an oral dose of 150 ng. chromic (Cr-51) picolinate in 0.51 ml. by gavage tube. An identical quantity of Cr-51 as chloride in acetate buffer was also administered to each of four rats. The rats had been fed standard lab chow prior to an 18 hr. fast and were given free access to food and water after administration of the isotopes. One hundred twenty hours after oral administration of the two forms of labeled chromium, each of the rats was killed by exsanguination after which the liver and kidneys were removed and cut into 1.0 g portions for assay of radioactivity content.

Results

The results obtained are listed in the following Table 1.

It will be seen from Table 1 that chromic tripicolinate is absorbed at a rate about 4 times greater than that of chromic chloride.

TABLE 1

| Form of isotope | Total radioactivity (CPM) in tissue | |
| --- | --- | --- |
| | Liver | Kidney |
| Chromic (Cr-51) Chloride | 30050 | 39030 |
| Chromic (Cr-51) Picolinate | 115075 | 157525 |

EXAMPLE 2

Protocol

In a toxicity experiment, rats weighing a mean of 223.4 g were given an oral suspension of 100 mg, 300 mg and 500 mg chromic tripicolinate in water. No deaths occurred and no visible effects were seen with any these oral doses. The tests were stopped at 500 mg because it was impossible to obtain a workable suspension beyond this level.

Results

These results indicate that the oral lethal dose of chromic tripicolinate is in excess of 2.2 g/Kg. Stated in human terms, a 70 Kg 154 pound) human would have to ingest a dose greater than 156 grams of chromic tripicolinate before any effects would be observed.

Three studies on human subjects were performed, as described in Examples 3 to 5 below, which illustrate the operation of the present invention.

EXAMPLE 3

Protocol

Subjects for the study were obtained after screening a group of volunteers. Thirty-two volunteers age 25-80 with total cholesterol levels of 5.7-8.3 mmoles/l (220-320 mg/dl) were initially chosen. No subject had a history of hypothyroid disease, renal failure, liver disease, diabetes mellitus, known familial lipid disorder, alcohol or drug abuse, bleeding disorders, multiple allergies or any other serious medical illness and none were pregnant at the outset. None of the subjects was using beta blockers, thiazide diuretics, steroids, chromium supplements or any investigational drugs. The volunteers were requested not to alter dietary or exercise habits during the course of the study. Informed consent was obtained and the subjects were paid a stipend for their participation.

Chromium tripicolinate was synthesized by first dissolving 2.66 g $CrCl_3 \cdot 6 H_2O$ in 25 ml warm (60° C.), deionized water. Thereafter, 3.69 g picolinic acid (Sigma Chemical, St. Louis, Mo., U.S.A.) was added and the contents were stirred with gentle heating until the solution turned purple and crystals began to form. The solution was then left standing at 4° C. overnight. The supernatant was then discarded and the crystals were airdried at room temperature. Analysis of the crystals indicated that the complex consisted of 3 moles picolinate/1 mole $Cr^{-3}$, MW=418.

For the double-blind, cross-over study, subjects were divided randomly into two treatment groups by a non-participant. During each half of the study participants ingested gelatin capsules that contained either chromic tripicolinate or a placebo. The chromic tripicolinate supplement contained 1.6 mg chromium tripicolinate (200 micrograms $Cr^{+3}$) mixed with 5 mg calcium phosphate. The placebo contained only 5 mg calcium phosphate. The study consisted of two 42-day periods with a 14-day period off capsules between treatments. Compliance by subjects was monitored by capsule count. The foregoing study protocol is illustrated in FIG. 1.

At the beginning, after three weeks and at the end of each period, heart rate, blood pressure, weight and temperature were measured and a fasting-blood sample was drawn. Serum parameters measured included total cholesterol, LDL-cholesterol, HDL-cholesterol, triglycerides, apolipoprotein $A_1$ and apolipoprotein B. Serum concentrations of cholesterol and triglycerides were determined with an Olympus 500 Automated Colormetric System (Olympus Instrument Co., Los Angeles, Calif., U.S.A.). HDL-cholesterol was assayed with an enzyme heparin-manganese chloride precipitation method (Albers et al., *Clin Chem.*, 1978; 24:853–856). LDL-cholesterol was estimated by the method of Friedwald (Friedwald, *Clin Chem.*, 1972; 18:499–502). Concentrations of apolipoprotein $A_1$ and apolipoprotein B in serum were assayed with a nephelometric immunoassay (Naito, *J. Clin. Immunol.*, 1986; 9:110–120) using a Boehringer laser kit.

Results

For statistical analysis of the measurements made in this study, the values obtained at the beginning and at the end of each 42-day period were used. Because each subject served as its own control, paired t tests were used to identify statistically significant differences between mean values of changes and differences in changes. Student's t test and p values were determiend with the program WORMSTAT ™ (available from Small Business Computers, New England, Conn., U.S.A.). The same type of statistical analysis was performed on the results of EXAMPLE 5 below. In all three studies of EXAMPLES 3, 4, and 5, p values less than 0.05 were considered statistically significant.

Figure 2:
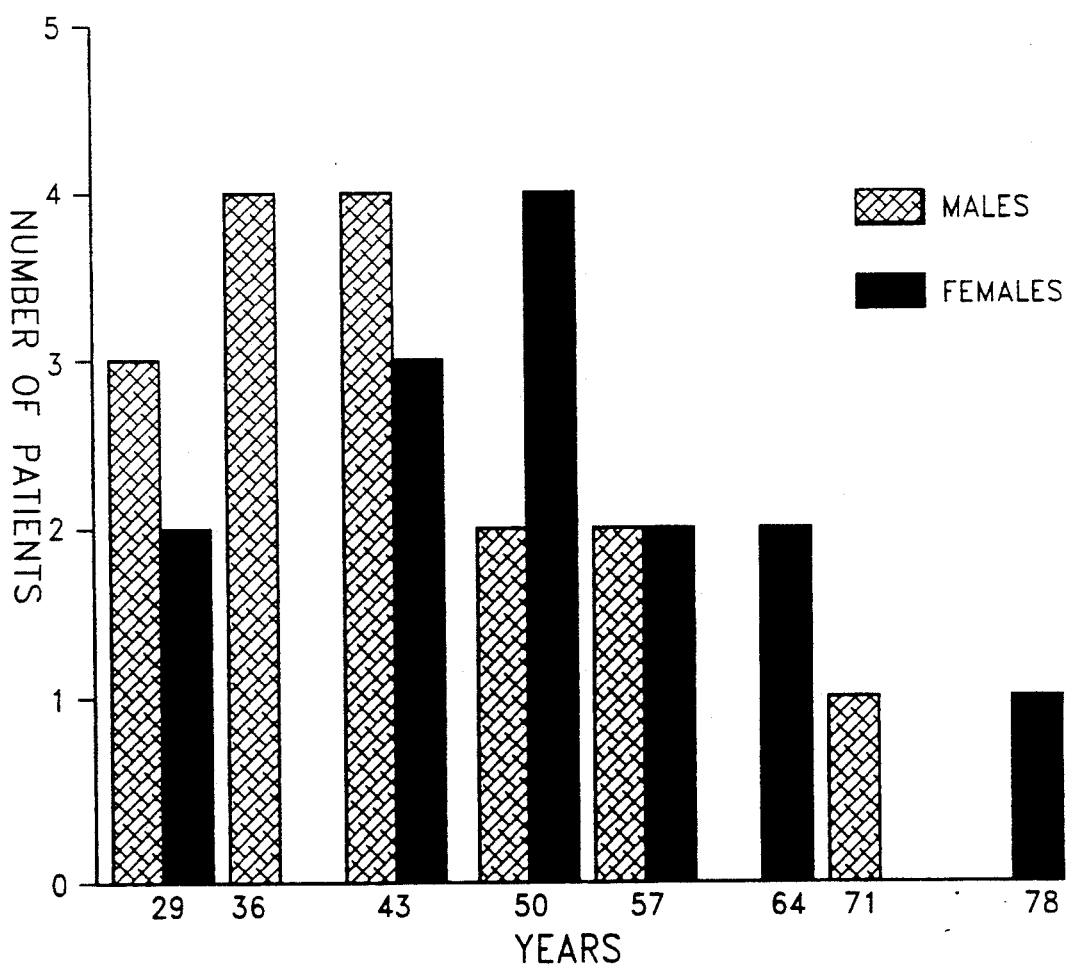
FIGS. 2 through 7, illustrate the values of various parameters measured during the study of EXAMPLE 3. and show the beneficial effect of chromic tripicolinate on serum lipids and glucose.
Figure 3:
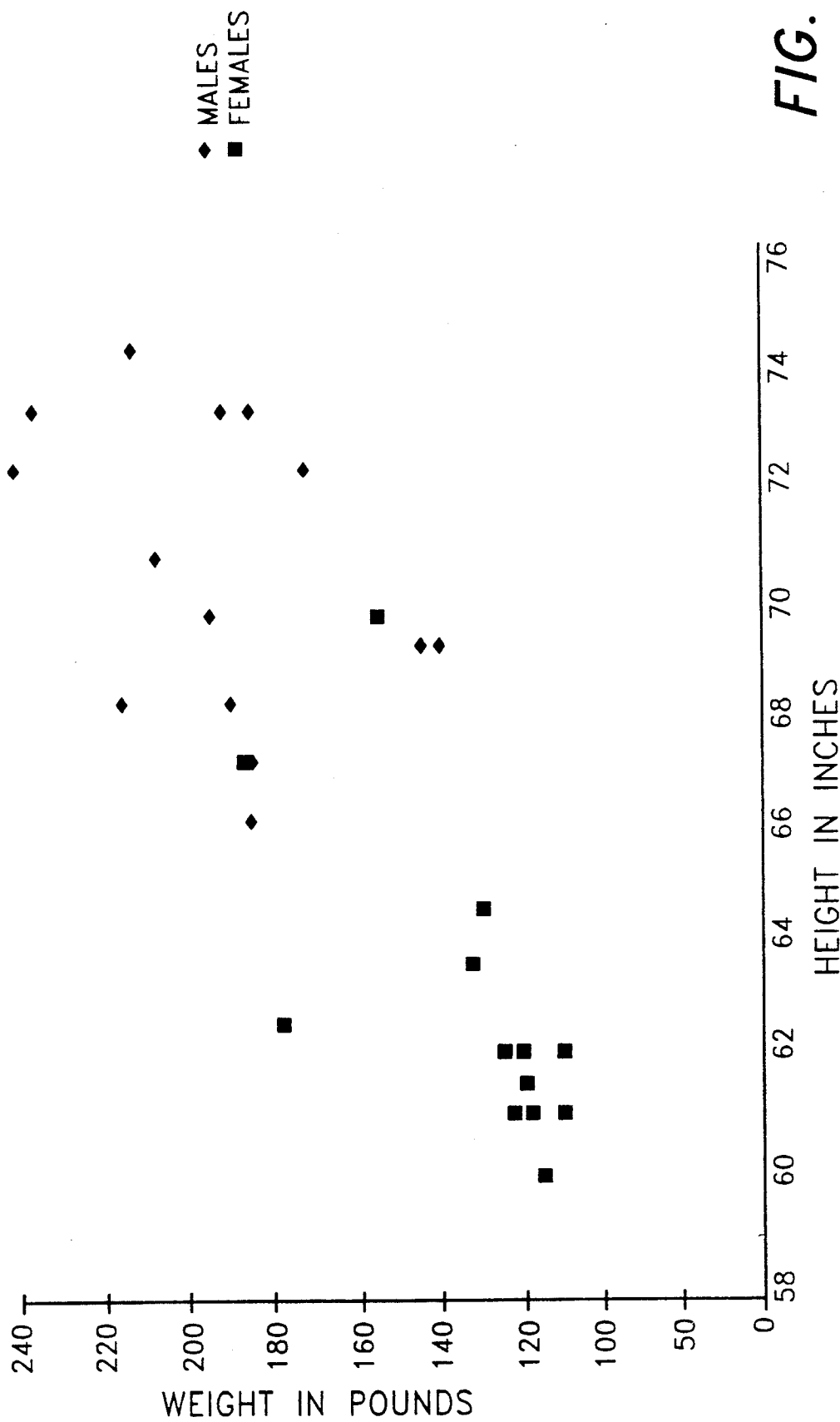

The mean age of the women in the study was 5 years greater than the male population (FIG. 2). Weight is reasonably correlated with height for the subjects in the study, as seen in FIG. 3. The inference is that the subjects who were studied appear to be representative of normal healthy population.

Of the original 32 participants in the study of EXAMPLE 3, 28 subjects completed the study. Two participants moved away, one became pregnant, and another (a 51 year old female) developed "hot flashes," elevated cholesterol levels and started menopause. Two subjects of EXAMPLE 3, developed mouth ulcers, one patient was on placebo and the other on chromium supplement. Three subjects developed a fine rash about their forearms; two subjects on placebo, one subject on chromium supplementation. No other abnormalities were noted.

Figure 4:
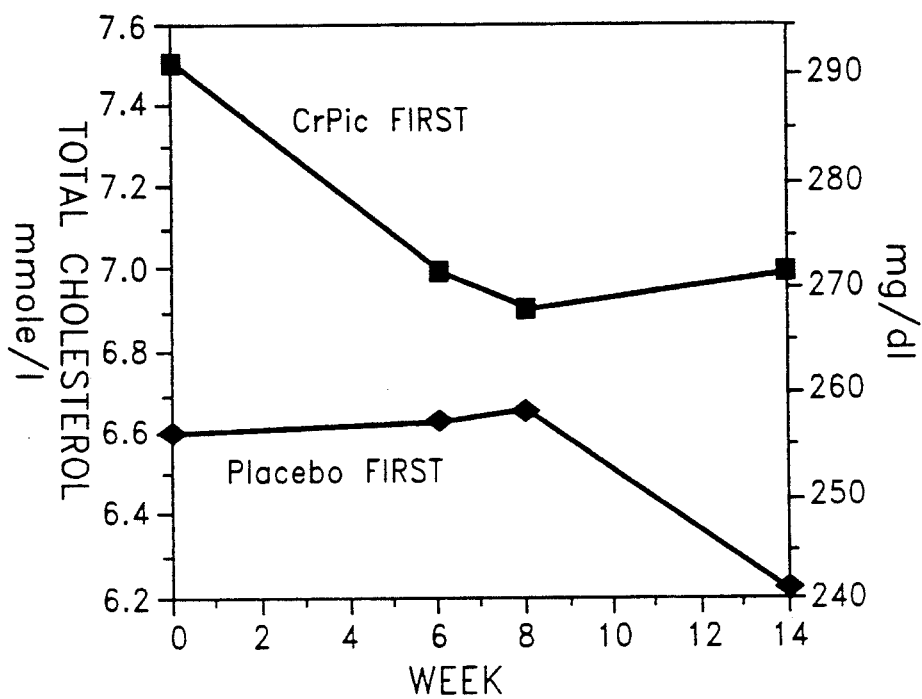
Figure 5:
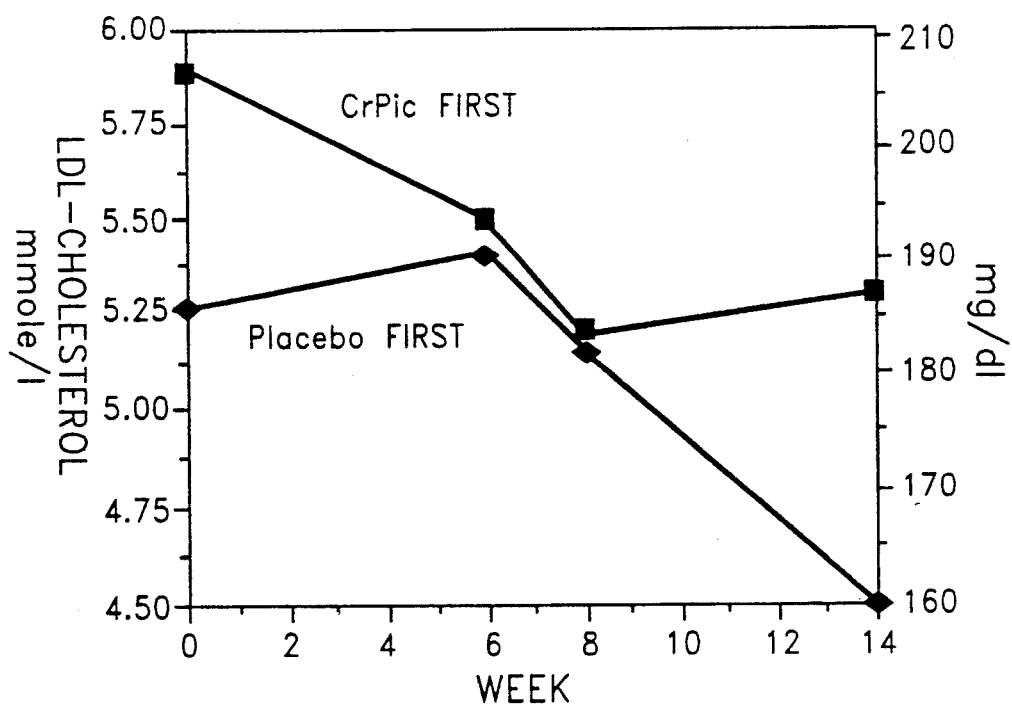
Figure 6:
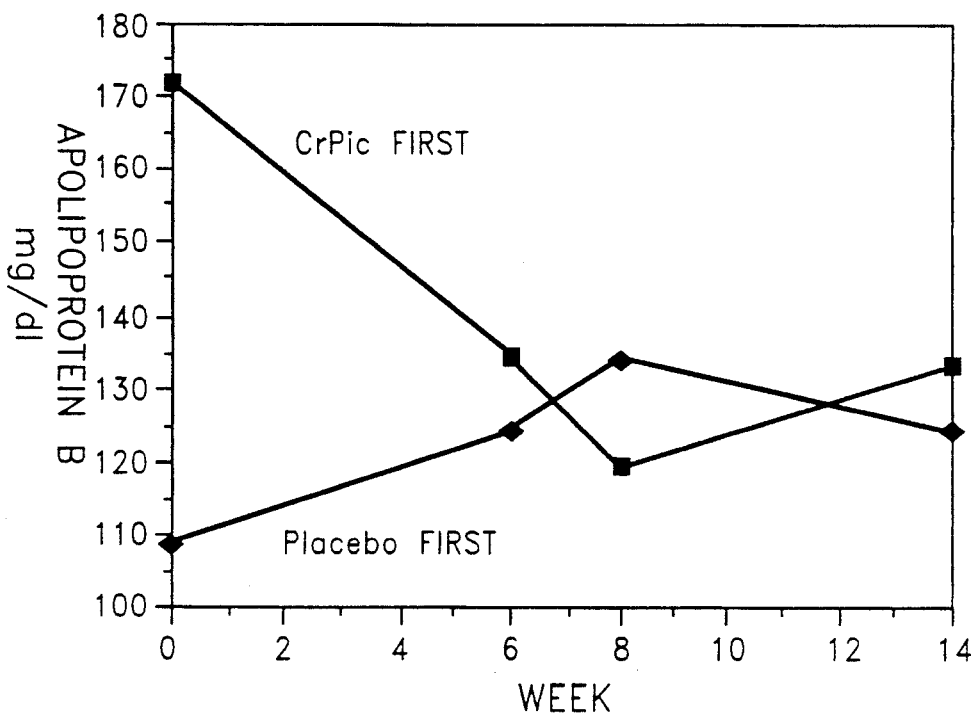

The results obtained after analysis of the serum cholesterol and serum apolipoprotein fractions are illustrated in FIGS. 4–7. As shown in FIGS. 4–6, total cholesterol, LDL-cholesterol and apolipoprotein B were all significantly decreased (p=0.007, p=0.015, and p=0.003, respectively) during the first 6-week period in subjects who began the study with the chromic tripicolinate supplement. No significant alterations (p>0.05) were observed in any of these serum parameters during the last 6-week period when the subjects were ingesting the placebo.

Figure 7:
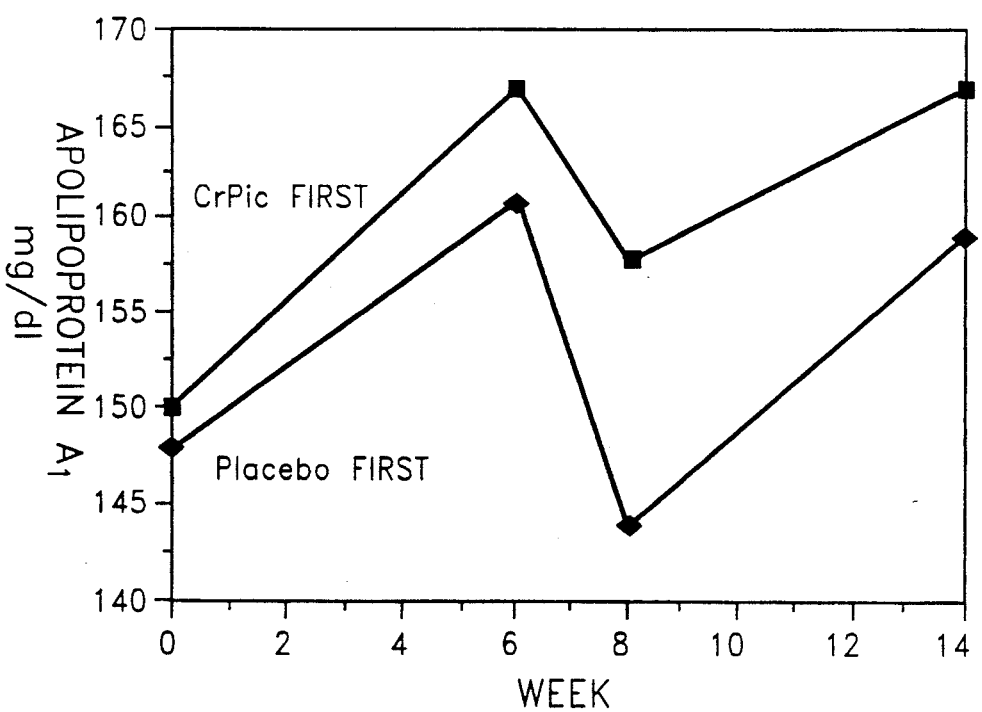

No significant change (p>0.05) was observed in either serum total cholesterol or LDL-cholesterol during the first 6-week period among the subjects who began the study with the placebo supplement. However, both total cholesterol and LDL-cholesterol decreased significantly (p=0.009 and p=0.003, respectively) during the final 42 days while these subjects were ingesting the chromic tripicolinate supplement (FIG. 4 and FIG. 5). In the group that began the study with the placebo, apolipoprotein B increased slightly, but not significantly (p=0.058) during the first 8 weeks and then decreased, but not significantly (p=0.072), after supplementation with chromic tripicolinate (FIG. 6). Apolipoprotein $A_1$ was significantly elevated (p=0.047) during the first 6-week period in the subjects that started the study with the chromic tripicolinate supplement. No significant change (p<0.05) was observed during the final 42 days. Apolipoprotein $A_1$ in the placebo-first group increased, but not significantly (p=0.165), during the first six weeks, and then decreased during the off-capsule period. During the chromic tripicolinate supplementation period, apolipoprotein $A_1$ was increased significantly (p=0.007) in these subjects (FIG. 7).

The consolidated results of the study are listed in Table 2 below. When the results from the 28 subjects were combined, significant (p<0.001) reductions occurred with both total cholesterol and LDL-cholesterol concentrations during the 42-day period that chromic tripicolinate was ingested. Total cholesterol concentration decreased 7% from 7.1 mmoles/l to 6.6 mmoles/l (276 mg/dl to 256 mg/dl) while LDL-cholesterol decreased 10.5% from 5.7 mmoles/l to 5.1 mmoles/l (200 mg/dl to 178 mg/dl) during treatment with chromic tripicolinate. Of the final 28 subjects, 22 had lower total cholesterol, 2 were unchanged and the remaining 4 had cholesterol concentrations elevated less than 0.1 mmole/l (5 mg/dl). With LDL-cholesterol, 20 subjects had decreased concentrations, 3 were unchanged and the others had slightly elevated concentrations of LDL-cholesterol. The concentration of serum HDL-cholesterol increased slightly but not significantly (p>0.05) during the period the subjects were ingesting chromic tripicolinate.

While subjects were ingesting the placebo, slight but statistically insignificant (p>0.05) elevations occurred in both serum total cholesterol and LDL-cholesterol.

When the volunteers were treated with chromic tripicolinate, the concentration of serum apolipoprotein B, the principal protein of the LDL-cholesterol fraction, was decreased significantly (p=0.001). Analysis of the values obtained from all 28 subjects showed a reduction of 16% from 155 mg/dl to 130 mg/dl. The principal protein of the HDL-cholesterol fraction, apolipoprotein A:, was significantly elevated (p=0.003) in the serum of subjects ingesting chromic tripicolinate.

During the period the subjects ingested the placebo, apolipoprotein B was elevated significantly (p>0.05). A slight, but not significant (p>0.05), elevation in apolipoprotein $A_1$ was also observed while the subjects were supplemented with the placebo. No significant changes were observed in serum triglycerides, weight, blood pressure, temperature or heart rate with either chromic tripicolinate or placebo.

Despite the fact that the supplements were distributed randomly, the concentration of each of the lipid parameters was consistently lower in the subjects at the start of the placebo supplementation period. By coincidence, the 14 subjects that started the trial with the placebo had serum lipids considerably lower than the 14 who started with chromic tripicolinate. Thus, because the mean levels of 14 subjects were initially lower coupled with the fact that the other 14 started with lower lipid levels resulting from successful treatment with chromic tripicolinate, the numerical means listed in Table 2 are less at the start of treatment with the placebo. As shown in FIGS. 4–7, regardless of the starting level, treatment with chromic tripicolinate produced significant changes.

The following parameters: Cholesterol, HDL, LDL, and hemoglobin $A_1C$ were tested initially, and at the end of each half of the study. Fasting blood sugars, blood pressure, weight and temperature were tested initially; at three weeks; and at the end of the study.

Glycosylated hemoglobin was measured by a modification of the method of Clegg and Schroeder (Clegg, et al. *J. Lab Clin. Med.*, 102:577–589, (1983)), using a Fast Hemoglobin Minicolumn, available from Isolab; Akron, Ohio, U.S.A.). Normal values are 5.5 to 7.5%. Fasting glucoses were measured by finger stick glucometer readings (using an Accucheck II from Boehringer Mannheim, Indianapolis, Ind., U.S.A.).

Split samples of cholesterol were sent to laboratories for analysis. Split samples of apolipoproteins were analyzed on a Beckman Array protein analyzer that was standardized by the Center for Disease Control, Atlanta, Georgia, U.S.A., using Lipid Research Clinic Guidelines (see *J. A. M. A.* 251: 351, (1984) and J. A. M. A. 251: 365, (1984)).

Results

For EXAMPLE 4, summary statistics are expressed as the mean ± standard error of the mean (SEM). Split-plot analyses of variance were used to assess treatment effects on the various parameters in the cross-over studies of variance (see Hills, et al., *Br. J. Clin. Pharmacol.* 8:7–20, (1979)). Correlation analysis was performed

TABLE 2

Serum lipid parameters after supplementation with chromic tripicolinate and placebo

| Serum Fraction | Chromic Tripicolinate | | | Treatment Placebo | | |
|---|---|---|---|---|---|---|
| | Init | Final | Chng. (P) | Init. | Final | Chng. (p) |
| Cholesterol Total | | | | | | |
| (mmole/l) | 7.1 ± 1.0 | 6.6 ± 1.0 | −0.5 | 6.8 ± 0.9 | 6.8 ± 1.0 | +0.1 |
| (mg/dl) | 276 ± 40 | 256 ± 41 | −19 | 262 ± 34 | 265 ± 38 | +3 |
| | | | p = .0003 | | | p = .282 |
| LDL | | | | | | |
| (mmole/l) | 5.7 ± 1.1 | 5.0 ± 1.0 | −0.6 | 5.2 ± 0.9 | 5.3 ± 0.8 | +0.1 |
| (mg/cl) | 200 ± 39 | 178 ± 35 | −21 | 184 ± 31 | 188 ± 30 | +4 |
| | | | p = .0003 | | | p = .106 |
| HDL | | | | | | |
| (mmol/l) | 1.3 ± 0.4 | 1.4 ± 0.4 | −0.1 | 1.4 ± 0.3 | 1.4 ± 0.4 | −0 |
| (mg/dl) | 52 ± 16 | 55 ± 17 | −3 | 53 ± 13 | 53 ± 17 | −.7 |
| | | | p = .118 | | | p = .369 |
| Apolipoproteins | | | | | | |
| Apo A (mg/dl) | 147 ± 28 | 163 ± 31 | +16 | 153 ± 26 | 164 ± 40 | +11 |
| | | | p = .003 | | | p = 0.77 |
| Apo B (mg/dl) | 155 ± 50 | 130 ± 45 | −25 | 115 ± 32 | 129 ± 36 | +14 |
| | | | p = .001 | | | p = .023 |
| Triglycerides | | | | | | |
| (mmol/l) | 1.9 ± 0.7 | 1.9 ± 0.9 | −0 | 1.9 ± 0.7 | 2.0 ± 1.0 | +0.1 |
| (mg/dl) | 168 ± 65 | 167 ± 76 | −1 | 165 ± 65 | 175 ± 88 | +10 |
| | | | p = .246 | | | p = .151 |

All values are mean ± SD of 28 subjects

EXAMPLE 4

Protocol

Eleven subjects with adult onset diabetes mellitus (AODM), participated in this study. These subjects had hemoglobin $A_1C$ concentrations greater than 9.0 and were on stable doses of oral hypoglycemic agents for four months. The participants received 200 micrograms chromium in the form of 1.6 mg chromium tripicolinate admixed with 5 mg of calcium phosphate, using the same protocol as in EXAMPLE 3 (FIG. 1). The dose of oral agent remained constant during the study.

with a linear regression curve-fitting program.

Figure 8:
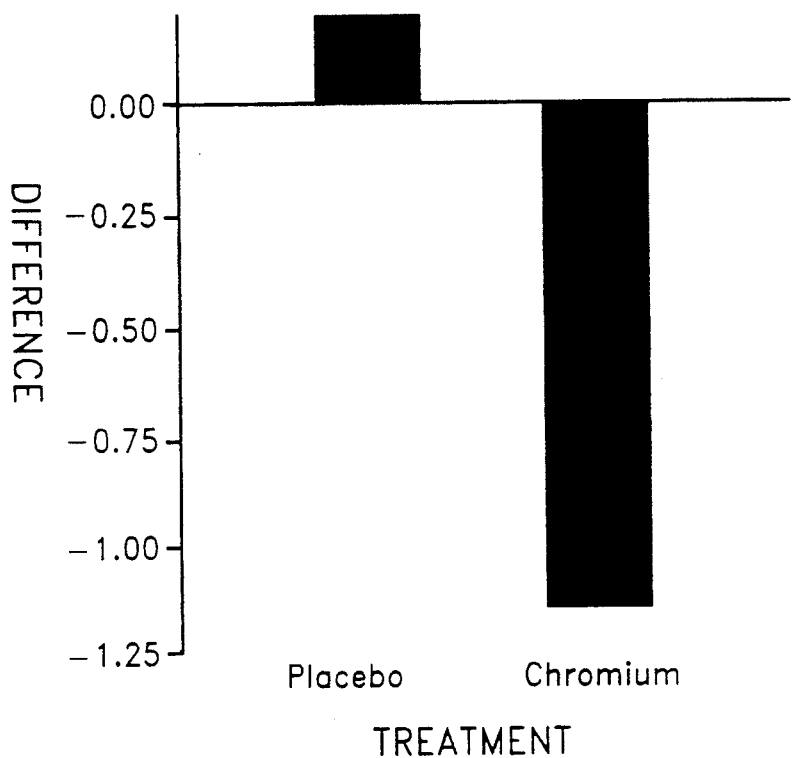
FIG. 8 and 9 illustrate the values of various parameters measured during another study on human subjects (EXAMPLE 4 below) which also show the beneficial effects of chromic tripicolinate
Figure 9:
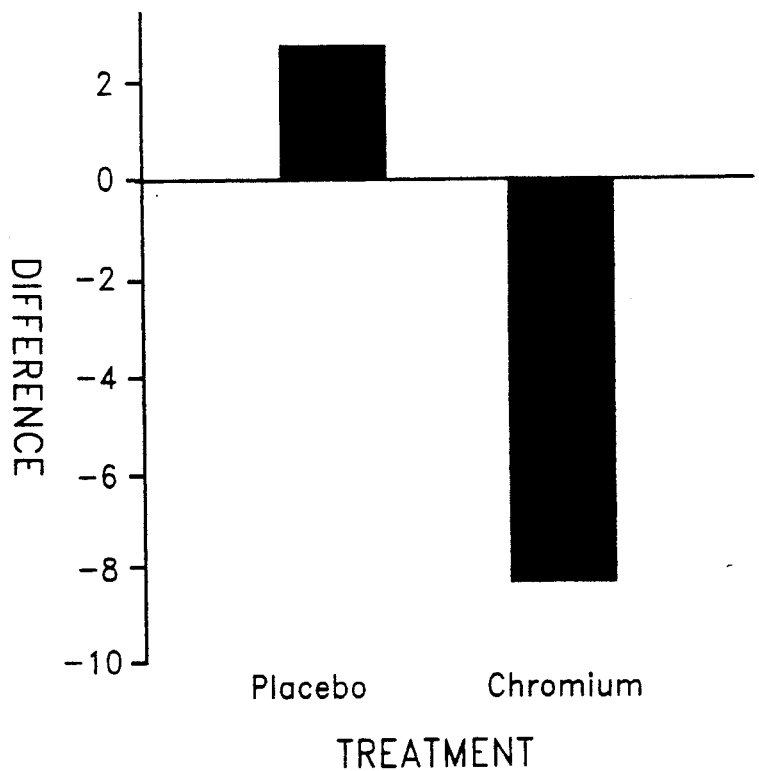

Analyses were performed on the following parameters for EXAMPLE 4: fasting blood sugars, hemoglobin $A_1C$, cholesterol, LDL, HDL, weight, blood pressure, heart rate and temperature. Results are summarized in Table 3. There were no significant changes in weight, blood pressure, heart rate, and temperature. HDL and cholesterol trends were favorable, but with the small sample studies P was not <0.05. Hemoglobin $A_1C$ significantly decreased 12% in the treatment versus placebo groups (FIG. 8). LDL significantly decreased by 8% (FIG. 9). All significant P values are <0.5.

TABLE 3

EXAMPLE 4: Effect of Supplemental Chromium Tripicolinate on 11 Subjects With Adult Onset Diabetes Mellitus Patients for the Parameters Listed.

| Parameter | Placebo | Cr Supplementation 6 Weeks |
|---|---|---|
| Cholesterol | 214.3 ± 12.2 | 211.4 ± 13.4 |
| LDL | 141.3 ± 9.4 | 139.5 ± 9.9 |
| HDL | 51.9 ± 6.0 | 52.3 ± 6.4 |
| Weight | 179.8 ± 9.4 | 179.6 ± 9.6 |
| Blood Pressure | 130.4/72.6 ± 5.4/3.4 | 132.9/72.4 ± 6.4/3.6 |
| Temperature | 97.5 ± .22 | 97.8 ± .11 |
| Heart Rate | 70.2 ± 2.2 | 70.1 ± 2.1 |
| Hemoglobin $A_1C$* | 10.8 ± 0.1 | 10.4 ± 0.1 |
| Fasting Bld Sugar* | 172.5 ± 12.9 | 162.2 ± 11.4 |

Values are given as mean ± standard error of the mean (SEM)
Level of significance was $p < 0.05$.
*Significant difference between placebo and chromium supplementation.

EXAMPLE 5

This study was performed to evaluate the anabolic effect of chromic tripicolinate in male subjects.

Protocol

At the start of the study, 10 male university students enrolled in weight training classes, were given, at random, a 40-day supply of capsules that contained either placebo (5 mg of calcium phosphate) or chromic tripicolinate (1.6 mg chromic tripicolinate admixed with 5 mg of calcium phosphate, which provided 200 ug of chromium). The identity of the capsules was known only to an individual who was not in any way involved in the study. During the 40-day period, each of the volunteers followed a prescribed weight lifting protocol for a total of 3 hours per week. Measurements taken at the beginning and again at the end of the study included various skin-fold thicknesses, biceps and calf circumferences, and body weight. Percent body fat was derived from the sum of the triceps, subscapular and chest skinfolds. Lean body mass was derived from anthropometrically-determined percent body fat: weight − (weight × percent body fat).

Results

Nine volunteers completed the study. Five of these were in the group given the placebo.

Figure 10:
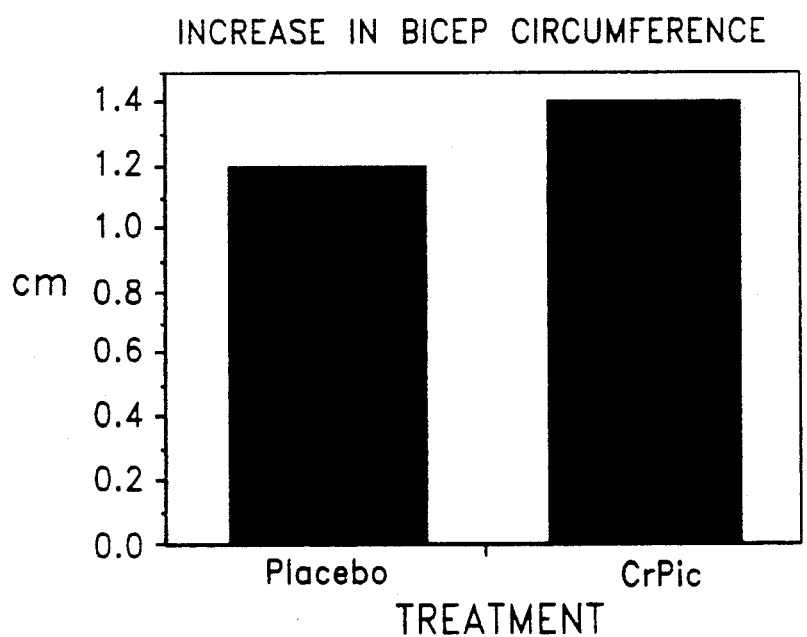
FIGS. 10-13 illustrate further test results from an additional human study (EXAMPLE 5 below) which show the anabolic effect of chromic tripicolinate.
Figure 11:
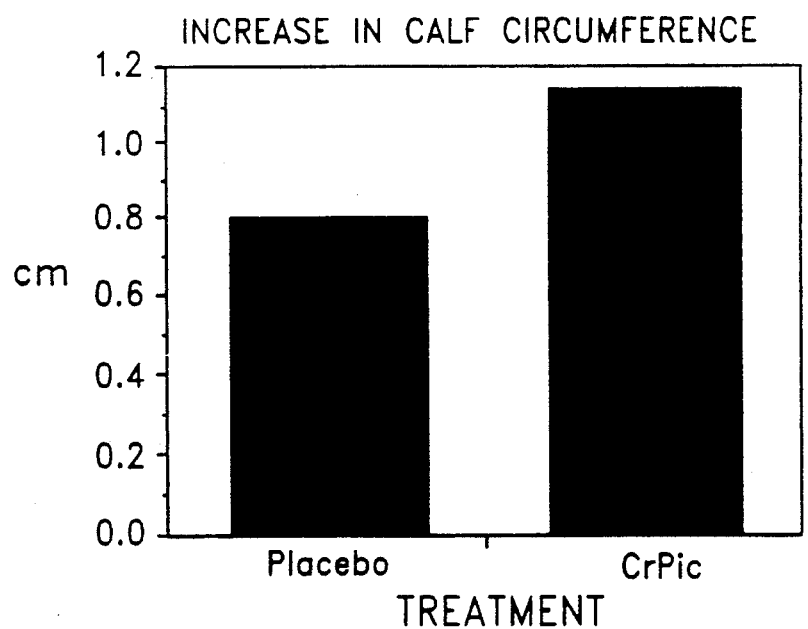
Figure 12:
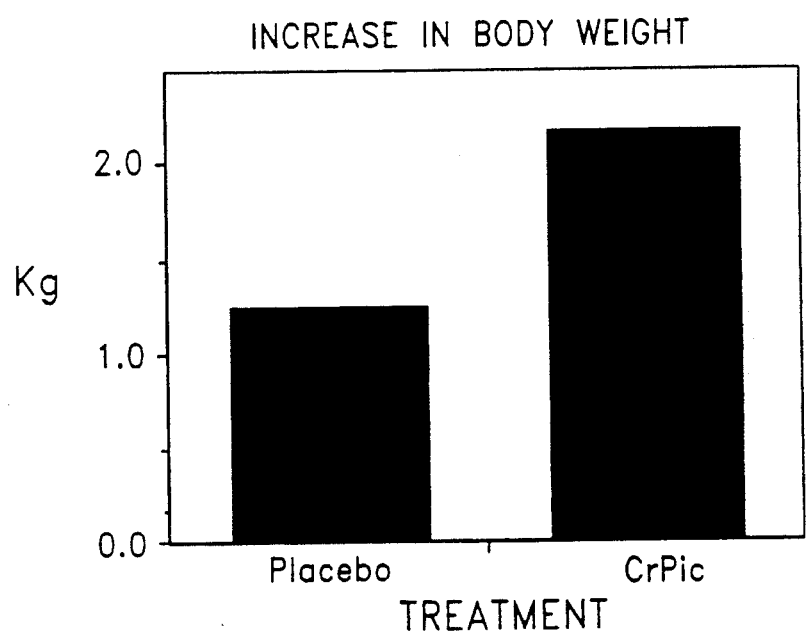
Figure 13:
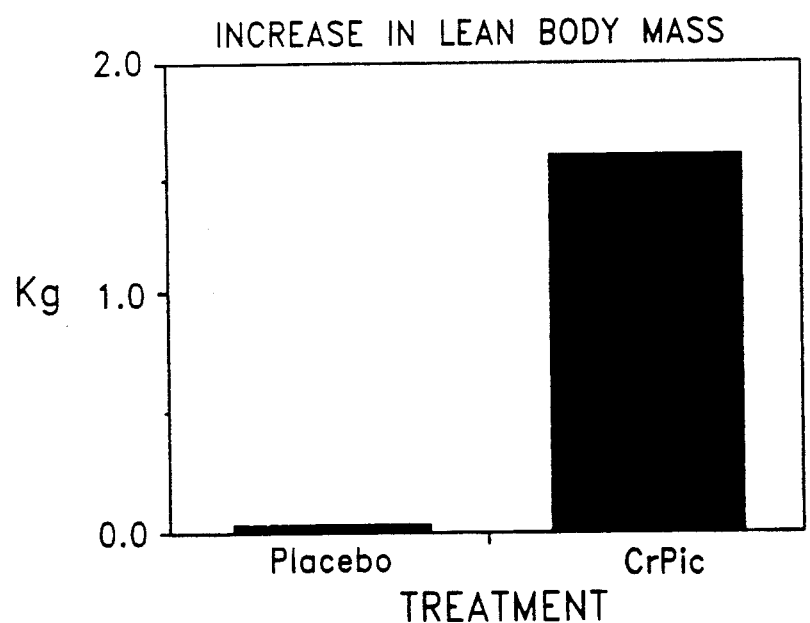

In the group consuming the placebo, bicep circumference increased significantly (P=0.017) 1.2±0.75 cm, while in the group given the chromic tripicolinate, the biceps circumference increased significantly (P=0.0056) 1.4±0.45 cm (see FIG. 10). In the placebo group, the calf circumference increased 0.82±0.88 cm which was not significant (P=0.067), while in the chromic tripicolinate group calf circumference increased significantly (P=0.029) 1.15±0.67 cm (see FIG. 11). In the placebo group, body weight increased significantly (P=0.0465) 1.25±1.14 kg, while the body weight of the group given chromic tripicolinate increased significantly (P=0.0325) 2.18±1.34 kg (see FIG. 12). In the placebo group, the calculated lean body mass increased only 0.04 kg which was not significant (P=0.464), while in marked contrast, the calculated lean body mass of the group given chromic tripicolinate increased significantly (P=0.017) 1.6 kg (see FIG. 13). Moreover, when the increase in lean body mass of the two groups was compared statistically by use of the independent variable Student's t test, the increase seen in the group given chromic tripicolinate was significantly greater (P=0.0198) than that of the placebo group.

The results obtained in EXAMPLE 3 demonstrate that chromic tripicolinate is an effective agent for the treatment of serum lipid disorders. The results of EXAMPLE 4 additionally demonstrate that chromic tripicolinate is effective in producing significant decreases in the levels of both fasting glucose and glycosylated hemoglobin in diabetic subjects. The results of EXAMPLE 5 demonstrate that chromic tripicolinate can act as an anabolic agent, thus implying that it can facilitate the entry of amino acids into skeletal muscles. Thus, chromic tripicolinate is a biologically active form of chromium. In addition, in the studies of Examples 3 and 4, four of the six serum lipid parameters measured were altered during the period the subjects ingested chromium. Total cholesterol, LDL-cholesterol and the related transport protein apolipoprotein B were decreased while apolipoprotein $A_1$, the HDL-cholesterol related protein, was elevated when the supplement contained chromic tripicolinate. Because each of these parameters is associated either directly or inversely to the onset of coronary artery disease, chromic tripicolinate is an excellent agent for consideration in the treatment and prevention of hyperlipidemia. It will be appreciated that compositions could be used in place of chromic tripicolinate which carry chromium ion and picolinate, provided that following administration to the individual, the chromium and picolinate can combine to form chromic tripicolinate.

Total cholesterol is a treatable risk factor for coronary heart disease (Lipid Research Clinics Program, JAMA, 1984; 251:351. Lipid Research Clinic's Program, JAMA, 1984; 251:365. Lipid Research Clinic's Program Epidemiology Committee Circulation, 1979; 60:127). During the 7.4 year Lipid Research Clinic's Coronary Primary Prevention Trial, an overall reduction of cholesterol of 8.5 percent was associated with a 19 percent decrease in coronary artery heart disease. Furthermore, the initial stages of atherosclerosis are directly related to the level of LDL-cholesterol (Newman et al., N. Engl J. Med., 1986; 314: 138-144). Both of these lipid fractions were decreased significantly after only 42 days of supplementation with chromic tripicolinate. Total cholesterol was reduced 7 percent while LDL-cholesterol was decreased 10 percent with this treatment.

Several recent studies additionally demonstrate that specific lipoproteins are associated with heart disease (Avogaro, et al., Artery. 1978; 4:385-394. Sniderman, et al., Proc. Natl. Acad Sci. USA, 1980; 77:604-608. Riesen, et al., Atherosclerosis, 1980; 37:157-162. DeBacker, et al., Atherosclerosis, 1982; 42:197-203. Maciejko, et al., N. Engl. J. Med., 1983; 309:385-389. Schmidt, et al., Am. J. Cardiol., 1985; 55:1459-1462. Kwiterovich, et al., Prev. Med., 1983; 12:815-834. Brunzell, et al., Arteriosclerosis, 1984; 4:79-83). In patients with documented coronary artery disease, elevated levels of apolipoprotein B coupled with reduced levels of apolipoprotein $A_1$ were observed. During our study, supplementation with chromic tripicolinate resulted in a significant elevation of apolipoprotein $A_1$ and a significant reduction in apolipoprotein B. Further, some investigators have suggested that levels of apolipoprotein $A_1$ and apolipoprotein B are a better predictor of coronary artery heart disease than levels of total, LDL, or HDL, cholesterol. (Kwiterovich, et al., suora.; and Brunzell, et al., suora.).

It is possible that higher doses of chromic tripicolinate than those used in EXAMPLE 3 above, may yield a greater reduction in total cholesterol. Additionally, there would be the possible potentiating effect of combining chromium with diet or different lipid-lowering agents. Further, use of higher doses of chromic tripicolinate than those used in Examples 3 and 4 may also enhance the beneficial effects found in those studies.

In order to reduce total serum cholesterol and LDL-cholesterol while at the same time increasing high density lipoprotein (HDL) cholesterol, it is anticipated that the dosage of chromic tripicolinate administered to a patient will contain between about 10 and about 200 micrograms of chromium, or more, with a dose of at least about 10 micrograms of chromium being administered. When chromic tripicolinate is administered as an anabolic agent, it is anticipated that the dosage will be approximately within the same range. The chromic tripicolinate may be orally ingested by way of a pharmaceutically acceptable carrier in, for example, tablet or capsule form. The chromic tripicolinate may typically be administered on a daily basis.

In order to reduce the requirement for insulin and/or diabetic drugs and reduce several important risk factors associated with maturity-onset diabetes, it is anticipated that the dosage range of chromium administered to a patient in the form of chromic tripicolinate will be between about 50 and about 500 micrograms, with a dose amount of at least about 50 micrograms of chromium being administered.

For the purposes of this invention, the compounds of the invention may be administered orally, parenterally, by inhalation spray, or by percutaneous diffusion in formulations containing conventional non-toxic pharmaceutically acceptable carriers, adjuvants and vehicles. The term parenteral as used herein includes subcutaneous intravenous, intramuscular, and intraarterial injection and infusion techniques. Intraarterial and intravenous injection as used herein includes administration through catheters. It is also anticipated that these compounds can be provided in the form of food additives.

Pharmaceutical compositions containing the active ingredient may be in any form suitable for the intended method of administration. When used for oral use, for example, tablets, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents selected from the group including sweetening agents, flavoring agents, coloring agents and preserving agents in order to provide a palatable preparation. Tablets containing the chromic tripicolinate in admixture with non-toxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents such as starch, gelatin or acacia; and lubricating agents, such as magnesium stearate, stearic acid or talc. Tablets may be uncoated or may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the chromic tripicolinate in admixture with excipients suitable for the manufacture of aqueous suspensions. Such excipients include suspending agents, dispersing or wetting agents, one or more preservatives, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to known art using suitable dispersing or wetting agents and suspending agents. The sterile injectable preparation may also be a sterile injectable solution or suspension in a non-toxic parenterally-acceptable diluent or solvent, such as a solution in 1,3-butanediol. Among the acceptable diluents and solvents that may be employed are water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

The amount of active ingredient that may be combined with the carrier material to produce a single dosage form will vary depending upon the host treated and the particular mode of administration.

The above description of the invention is set forth solely to assist in understanding the invention. It is to be understood that variations of the invention, including all equivalents now known or later developed, are to be considered as falling within the scope of the invention, which is limited only by the hereafter appended claims.

We claim:

1. A method for treating undesirable high levels of blood serum lipids in an individual in need of such treatment, comprising the administration of an effective blood serum lipid-reducing amount of a composition consisting essentially of chromic tripicolinate.

2. A method for treating undesirable high levels of blood serum lipids in an individual in need of such treatment, comprising the administration of an effective, blood serum lipid reducing amount of chromic tripicolinate.

3. A method for treating undesirable high levels of blood serum lipids in an individual, comprising:
   a) evaluating the individual for undesirable high levels of blood serum lipids; and
   b) then, when the evaluation indicates undesirable high levels of blood serum lipids, administering an effective, blood serum lipid reducing dose of chromic tripicolinate.

4. The method of claim 2 wherein said chromic tripicolinate is in a pharmaceutically acceptable carrier and is orally ingested.

5. The method of claim 2 wherein said chromic tripicolinate is present in a pharmaceutically acceptable carrier in a dose having at least about 10 micrograms of chromium.

6. The method of claim 2 wherein said chromic tripicolinate is present in a pharmaceutically acceptable carrier in a dose having from about 10 to 200 micrograms of chromium.

7. The method of claim 3 wherein said chromic tripicolinate is substantially pure.

8. The method of claim 3 wherein said chromic tripicolinate is substantially free of impurities from brewer's yeast.

9. The method of claim 3 wherein said chromic picolinate is synthetic chromic tripicolinate.

10. The method of claim 3 wherein said blood serum lipids are serum triglycerides.

11. The method of claim 3 wherein said blood serum lipids are total serum cholesterol.

12. The method of claim 3 wherein said blood serum lipids are LDL-cholesterol.

13. The method of claim 3 wherein a known dose of chromic tripicolinate is administered on each of a plurality of days, the method additionally comprising reevaluating the level of blood serum lipids.

14. The method of claim 13 wherein the administration of chromic tripicolinate is continued until the re-evaluation indicates a decrease in blood serum lipids.

15. A method for treating undesirable high levels of blood serum lipids in an individual, comprising:
   a) evaluating the individual for undesirable high levels of blood serum lipids; and
   b) then, when the evaluation indicates undesirable high levels of blood serum lipids, administering an effective blood serum reducing amount of chromium ion and picolinate ion such the two can form chromic tripicolinate in the individual.

16. The method of claim 15 additionally comprising re-evaluating the level of blood serum lipids, wherein chromium ion and picolinate are administered on each of a plurality of days prior to the re-evaluation until the re-evaluation indicates a decrease in blood serum lipids.

17. A method for increasing blood serum levels of HDL-cholesterol in an individual in need thereof, comprising the administration of an effective amount of chromic tripicolinate.

18. A method for increasing an undesirable low level of blood serum HDL-cholesterol in an individual, comprising:
   a) evaluating the individual for the undesirable low level of blood serum HDL-cholesterol; and
   b) then, when the evaluation indicates an undesirable low level of blood serum HDL-cholesterol, administering an effective HDL-cholesterol increasing dose of chromic tripicolinate.

19. The method of claim 18 wherein said dose of chromic tripicolinate is administered on each of a plurality of days, the method additionally comprising re-evaluating the blood serum HDL-cholesterol level, the administration of chromic tripicolinate being continued until the re-evaluation indicates an increase in blood serum HDL-cholesterol.

20. A method for lowering blood serum LDL-cholesterol in an individual in need of such reduction, comprising the administration, over a plurality of days, of chromic tripicolinate in a dose having at least about 10 micrograms of chromium per day.

21. A method for lowering blood serum LDL-cholesterol in an individual in need of such reduction, comprising:
   a) evaluating the individual's blood serum LDL-cholesterol level; and
   b) then administering, over a plurality of days, a composition consisting essentially of chromic tripicolinate in a dose having at least about 10 micrograms of chromium per day;
   c) then re-evaluating the individual's blood serum LDL-cholesterol level.

22. The method of claim 21 wherein the administration of chromic tripicolinate is continued until the re-evaluation indicates a decrease in blood serum LDL-cholesterol.

23. The method of claim 21 wherein said chromic tripicolinate is in a pharmaceutically acceptable carrier and is orally ingested.

24. A method for lowering blood serum LDL-cholesterol in an individual in need of such reduction, comprising:
   a) evaluating the individual's blood serum LDL-cholesterol level; and
   b) then administering, over a plurality of days, a composition consisting essentially of a chromium ion containing compound and a picolinate containing compound, in a manner such that the two can form chromic tripicolinate in the individual, and in an amount sufficient such that a dose of chromic tripicolinate having at least about 10 micrograms of chromium per day is provided to the individual;
   c) then re-evaluating the individual's blood serum LDL-cholesterol.

25. A method for the prevention of undesirable high levels of blood serum lipids in a patient in need thereof, comprising the administration to said patient of substantially pure chromic tripicolinate in a dose having at least about 10 micrograms of chromium per day.

26. The method of claim 25 wherein said chromic tripicolinate is in a pharmaceutically acceptable carrier and is orally ingested.

27. The method of claim 25 wherein said blood serum lipids are triglycerides.

28. The method of claim 25 wherein said blood serum lipids are total serum cholesterol.

29. The method of claim 25 wherein said blood serum lipids are LDL-cholesterol.

30. The method of claim 1, wherein at least about 200 µg chromium as chromic tripicolinate are administered each day for a plurality of days.

31. The method of claim 17, wherein at least about 200 µg of chromium as chromic tripicolinate are administered each day for at least about 40 days.

* * * * *